United States Patent

Imaino et al.

[11] Patent Number: 5,867,261
[45] Date of Patent: Feb. 2, 1999

[54] SURFACE INSPECTION TOOL

[75] Inventors: Wayne Isami Imaino; Anthony Juliana, Jr.; Milton Russell Latta; Charles H. Lee; Wai Cheung Leung, all of San Jose; Hal J. Rosen, Los Gatos, all of Calif.

[73] Assignee: International Business Machines Corporation, Armonk, N.Y.

[21] Appl. No.: 840,352

[22] Filed: Apr. 28, 1997

[51] Int. Cl.⁶ ................................................. G01N 21/88
[52] U.S. Cl. ................................. 356/237.2; 356/243.4; 348/128
[58] Field of Search ................................. 356/237, 239, 356/243, 394, 429–431, 375; 250/234, 235, 236; 359/216, 217, 218, 219; 348/125, 128, 129

[56] References Cited

U.S. PATENT DOCUMENTS

| | | | |
|---|---|---|---|
| 3,790,287 | 2/1974 | Cuthbert et al. | 356/120 |
| 4,358,202 | 11/1982 | Puffer et al. | 356/430 |
| 4,464,050 | 8/1984 | Kato et al. | 356/237 |
| 4,522,497 | 6/1985 | Ikin | 356/243.4 |
| 4,610,541 | 9/1986 | Tanimoto et al. | 356/237 |
| 4,794,265 | 12/1988 | Quackenbos et al. | 250/572 |
| 4,861,164 | 8/1989 | West | 356/445 |
| 4,954,723 | 9/1990 | Takahashi et al. | 250/572 |
| 5,076,692 | 12/1991 | Neukermans et al. | 356/538 |
| 5,125,741 | 6/1992 | Okada et al. | 356/237 |
| 5,220,617 | 6/1993 | Bird et al. | 356/237 |
| 5,317,380 | 5/1994 | Allemand | 356/431 |
| 5,381,225 | 1/1995 | Kohno | 356/237 |
| 5,448,364 | 9/1995 | Moran | 356/430 |
| 5,523,846 | 6/1996 | Haga | 356/445 |
| 5,528,360 | 6/1996 | Kohno | 356/237 |
| 5,530,548 | 6/1996 | Campbell et al. | 356/375 |

FOREIGN PATENT DOCUMENTS

| | | | |
|---|---|---|---|
| 59-73710 | 4/1984 | Japan | G01B 11/30 |
| 1257250 | 10/1989 | Japan | G01N 21/88 |
| 0132311 | 5/1990 | Japan | G01B 11/24 |

OTHER PUBLICATIONS

IBM TDB vol. 19, No. 12, May 1977 "Surface Optical Reflectance Process Monitor" By C. Kircher et al.
IBM TDB vol. 30, No. 7, Dec. 1987 Dual Laser Reflective Scanner By D. Forslund et al.
IBM TDB vol. 20, No. 3, Aug. 1977 "Visually Aligned Monochromatic Lamina Detector" By C. Gaston et al.
IEEE/Semi 1995 Advanced Semiconductor Manufacturing Conference and Workshop Nov. 13–15, 1995.

Primary Examiner—Hoa Q. Pham
Attorney, Agent, or Firm—G. Marlin Knight

[57] ABSTRACT

A laser based inspection tool (LIT) for inspecting planar surfaces is described. In a preferred embodiment the LIT can simultaneously inspect both planar surfaces of disks for use in disk drives. The LIT uses a mechanical lifter which moves the disk through the laser scan lines (i.e. perpendicular to the scan lines) to allow the entire surface on each side of the disk to be scanned. The light reflected from the surface is routed to a detector which converts the intensity of the reflected beam into an analog signal. The analog signal is sampled and digitized to generate pixel data. A data acquisition system sequentially stores the pixel data in a buffer. The edges of the planar surface in the pixel data are determined for each scan line while data acquisition is in progress. A mask is applied to direct the defect detection only to meaningful areas of the disk while data acquisition is in progress. A median filter and derivative analysis can be applied to the pixel data to detect deviations indicating defects. An optional calibration mirror is taught which is positioned to reflect substantially all of the incident beam during a segment of the scan line as the reflected calibration beam which is converted to an analog signal, sampled and digitized similarly to the reflected beam from the surface being inspected. By comparing the intensity of the calibration beam to the reflected beam the reflectivity of the surface can be measured.

20 Claims, 10 Drawing Sheets

SURFACE INSPECTION TOOL

RELATED APPLICATIONS

Commonly assigned, related applications with Ser. No. 08/840,351; 08/841,214; 08/840,358; 08/841,037; 08/840,339 and 08/840,354 were filed concurrently with this application.

FIELD OF THE INVENTION

The invention relates to the field of precision surface analysis for defects. More particularly the invention relates to laser based tools for obtaining data on surface features by optical means.

BACKGROUND

Magnetic and optical disks require precision surfaces with extremely low defect rates to function properly. A typical magnetic disk comprises a substrate on which multiple layers of various materials are deposited. For example, an aluminum substrate might be coated electrolessly with NiP then sputtered with thin films of Cr as an undercoat, a cobalt alloy magnetic layer and a hydrogenated carbon overcoat. Depending on the stage of the process these surfaces are not necessarily uniform. For example, after the NiP has been applied a small circular band on the surface of the disk may be textured using a laser to form microscopic bumps. This textured region is intended to provide a low stiction area for the sliders to rest during nonoperating periods. In addition to intentional variations there may be various types of defects. As the disks progress through the manufacturing process various tests and inspections are used to detect defective disks so that they may either be reworked or discarded. In addition to visual inspections, a disk may be subjected to glide tests which are sensitive to the flatness of the planar surfaces, as well as magnetic read/write tests. Due to high capacities of magnetic disks it is typically not practical to magnetically test each bit which can be stored on the disk.

Laser surface inspection of the disks if sufficiently precise may actually be superior to current magnetic tests in detecting defects. Magnetic defects are usually associated with visible defects, but the visible defects can be detected more efficiently through laser inspection even though the laser spot size is considerably larger than the area in which a bit can be recorded. Thus, laser inspection allows greater test coverage of the disk in a cost effective manner.

Various laser inspection devices are known in the art. Commonly assigned U.S. Pat. No. 5,220,617 by Bird, et al. describes a laser scanner for green sheets to detect via errors. The sheets are moved on an air track to a transport table which translates them as the scan occurs. Only one side is scanned. The system uses a rotating polygon mirror to scan and to capture the reflected light. The bright field reflected light is captured at the hole-in-plate splitter and directed to a single fiber. This channel detects contrast between the conductive paste and the green sheet. The dark field light reflected light is captured by fibers located near the surface of the object. The incident light is perpendicular, but there is a suggestion that other angles are possible. There is a start of scan mirror adjacent to the object, but its function is said to be to provide an initialization or start/stop point. The reference signal is obtained from the initial part of the green sheet. The lens assembly is a flat field telecentric anamorphic f-theta lens system. The f-theta condition corrects for the pincushion distortion. A focusing telescope converges the image down to a slit. The shaping lens system results in a collimated bundle 10.8 mm by 130 microns on the polygon. This shape is said to be selected for pickup by the fiber bundles.

SUMMARY OF THE INVENTION

The inventions will be described as embodied in a laser based inspection tool (LIT) for simultaneously inspecting both planar surfaces of disks for use in disk drives. The LIT uses low angle reflected light rather than scattered light from the surface to simplify the design, to allow absolute reflectivity measurements if desired and to aid in the detection of certain types of disk defects such as stains. Since the surfaces of the disks are extremely sensitive to physical contact the LIT uses a mechanical lifter which, without clamping or spinning, moves the disk through the laser scan lines to allow the entire surface on each side of the disk to be scanned. Inspection or test systems which require the disks to spin are complex and increase the risk of damage to the disk. The line scanning is performed using a rotating polygonal mirror (scanner) which also captures the beam reflected from the disk surface. A telecentric lens assembly (TLA) acts to ensure that the laser beam is incident at a constant nearly perpendicular angle as the beam scans across the disk. The TLA is designed to have a very flat field curvature through the scanning line to keep the spot size sufficiently constant for accurate detection. A small deviation from perpendicular incidence in the cross-scan direction allows the reflected beam from the disk to be separated from the incident beam for detection and analysis. The rotational position of the two polygonal scanners are synchronized, but with one being angularly displaced to avoid interference when the beams scan across the hole in the center of the disk.

The reflected light is digitized and stored in a memory accessible by a computer. The edges of the disk are detected and a mask is applied to direct the defect detection only to meaningful areas of the disk. The techniques for detecting defects include use of a median filter and derivative analysis.

DETAILED DESCRIPTION OF THE PREFERRED EMBODIMENTS

The preferred embodiments of the inventions will be described in relation to a laser based inspection tool for inspecting the planar surfaces of disks for use in disk drives. The inspection may be performed on substrates or finished disks and is preferably performed on both surfaces of the disk simultaneously. The Laser Inspection Tool (LIT) is general in that it can be used to inspect any sufficiently smooth flat surface at any stage of the process; therefore, it could be used to inspect raw or initial substrates, substrates after nickel-phosphorous coating, or finished disks. The LIT uses low angle reflected light rather than scattered light from the surface to simplify the design, to allow absolute reflectivity measurements if desired and to aid in the detection of certain types of disk defects such as stains which do not effect the scattering of the light. Stain detection is accomplished through the use of derivative analysis of the reflected light to detect the change in the reflectivity of the surface associated with a disk stain. The system is designed to preserve both the polarization and the wave vector of the reflected light which allows it to be used with minor modifications in a broad range of applications. Using a stable laser, low noise detectors and sufficiently high resolution A/D converters, it is possible to detect a change in reflectivity of approximately 0.1% using the LIT. Since the surfaces of the disks are extremely sensitive to physical contact the LIT uses a mechanical lifter which, without clamping or spinning, moves the disk through the laser scan lines to allow the entire surface on each side of the disk to be scanned. Inspection or test systems which require the disks to spin are complex and increase the risk of damage to the disk. The line scanning is performed using a rotating polygonal mirror (scanner) which also captures the beam reflected from the disk surface. As the disk is lifted into the scanning area it passes through a pair of air knives which blow loose particles from both surfaces.

Figure 1:
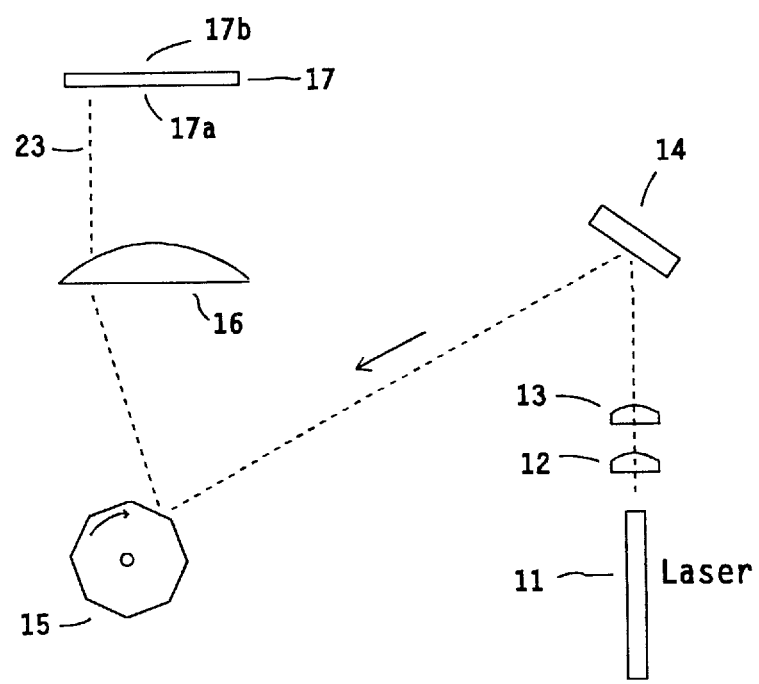
FIG. 1 shows the optical elements in the path from the laser source to the surface to be inspected.

FIG. 1 shows the optical path elements for the optical system of one channel (the A-channel) of the LIT from the laser source 11 to the disk 17 and the disk surface to be inspected 17a in a preferred embodiment. The elements in the second channel (the B-channel) for inspecting the other surface 17b are identical, but are preferably arranged in a mirror image of the A-channel elements and in the same plane. The A and B-channels can be assembled on a single baseplate. The choice of low power laser is not critical, e.g. GaAs, HeNe, etc. are acceptable, but it is preferable that the wavelength be in the visible spectrum for aiding alignment. The use of an unpolarized laser is preferable, since it reduces sensitivity to the orientation of defects such as scratches. A few milliwatts of power is sufficient. Since high sensitivity to absolute amount of reflected light is a goal in the design of the LIT, it is important to select a laser, e.g. HeNe, to minimize noise which might be injected into the system through laser instability. In the preferred embodiment separate lasers are used for each channel, but it is also possible to use a single laser source with a beam splitter. Lenses 12 and 13 form a telescope (beam expander) which is used to expand the beam 23 (the incident beam). The term incident beam (or A-beam to specify the A-channel) will be used to refer to all segments of the laser beam from generation at the laser 11 along the path to the surface of the disk being inspected (or as will be noted later an optional calibration mirror). Steering mirror 14 reflects the beam onto the rotating polygon scanner 15 which reflects into the telecentric lens assembly (TLA) 16. The TLA acts to keep the laser beam incident at a constant nearly perpendicular angle as the beam scans across the disk. The TLA is designed to have a very flat field curvature through the scanning line to keep the spot size sufficiently constant for accurate detection. The figure shows the polygon scanner 15 rotating in a clockwise direction which will cause the incident beam to sweep from left to right across the TLA and in turn to scan a line across the planar surface of the disk. Each mirrored facet of the polygon corresponds to one scan line across the disk. The choice of a polygon scanner is preferred, but other scanning means such as a galvonometer mirror could be used. The view of FIG. 1 can be considered to be a top view which shows only the top edge of the disk or other item having the planar surface to be inspected. The TLA should have a usable optical scan line which is at least equal to and preferably slightly longer than the desired scan length. A laser spot size on the disk of approximately 50 microns in diameter provides sufficient resolution for detecting defects in current disks. Smaller spot size can be used to increase the maximum resolution of the system if desired by altering the focal lengths of the telescope lenses.

Figure 2:
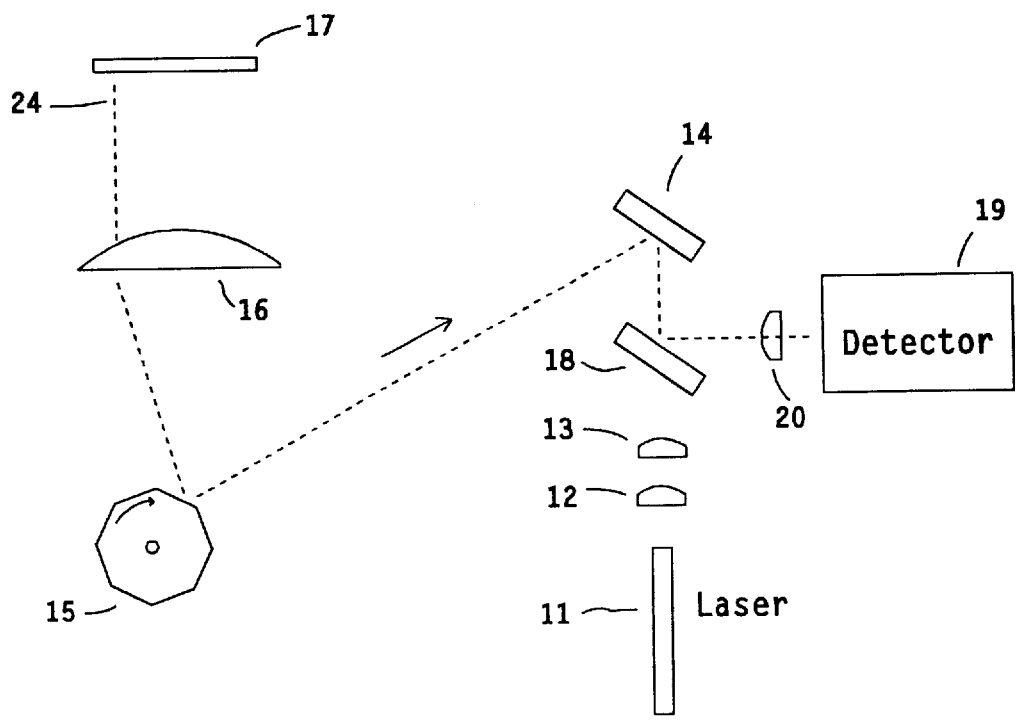
FIG. 2 shows the optical elements in the path for the reflected laser light from the surface being inspected.

FIG. 2 shows the optical elements in the path for the reflected beam 24 from the surface being inspected. The term reflected beam (or A/R-beam) will be used to refer to all segments of the beam which is reflected from the object's surface as it follows the path to the detector. The surface of the object 17 reflects a portion of the incident beam to form a reflected beam 24 which follows a path back through the LIT which is slightly offset from the path of the incident beam. (Note: The described embodiment inspects the planar surfaces of disks, but nonplanar surfaces could be inspected using the system if the nonplanarity is no more than a few degrees.) The reflected beam passes through the TLA 16 and is reflected by the scanner 15 back to mirror 14. Because the path of the reflected beam is offset from the incident beam the reflected beam strikes capture mirror 18 which diverts the reflected beam through lens 20 which reduces the spot size of the beam striking detector 19. The detector is preferably a silicon detector which produces an analog signal which is a function of the amplitude of the reflected beam. The detector should have very low noise to preserve the sensitivity of the system. The LIT may function by detecting only relative shifts in the reflected beam as it scans across the surface and as the surface is translated under the beam, but it is advantageous to detect absolute reflectivity. The use of reflected light for inspection rather than scattered light allows a simplified approach and avoids the problems involved in trying to capture all of the scattered light. In addition the use of reflected light allows detection of absorption changes and defects associated therewith.

Figure 3:
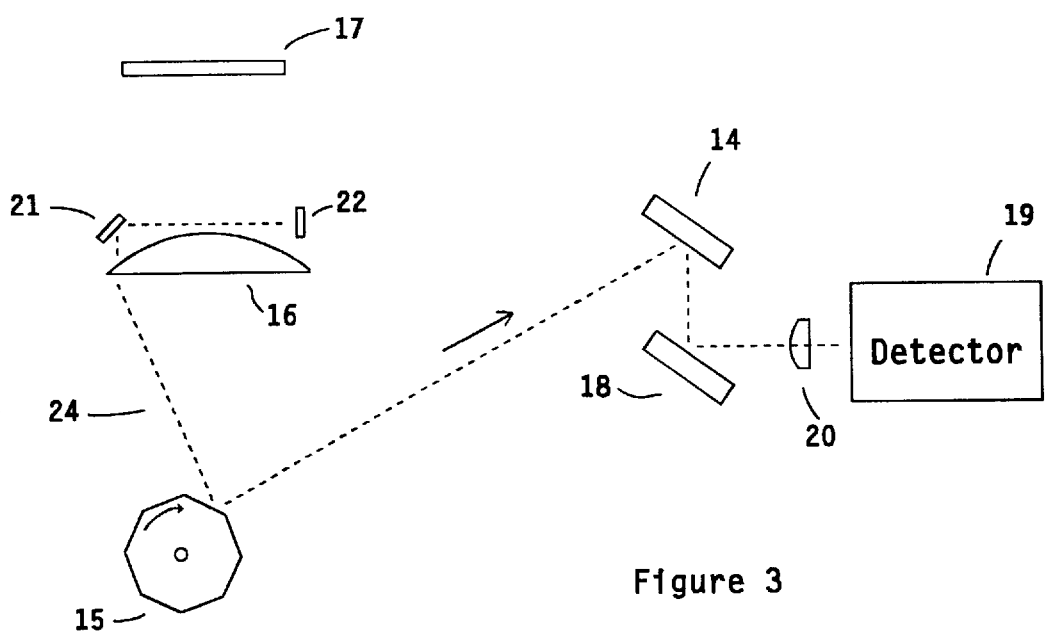
FIG. 3 shows the optical elements in the path for the reflected laser light from the calibration mirrors.

FIG. 3 shows an optional feature which provides a start of scan signal and allows the detector to be calibrated to measure the absolute amplitude of the reflected beam. Measurement of the absolute reflectivity allows an additional class of defects and/or characteristics to be detected and/or measured, thus enhancing the capability of the tool. Calibration mirrors 21 and 22 are arranged so that an initial portion of the scan line falls on mirror 21 which reflects the beam to mirror 22 which reflects the beam back to mirror 21 and back into the TLA along the path for the reflected beam as described above. The length of the path of the beams going to and from the calibration mirrors is set equal to the length of the beam paths to and from the surface 17 to prevent spot size change. This arrangement creates a reference signal from the detector for each scan line which signals the start of the scan and is also known to correspond to maximum possible magnitude of the reflected beam. Alternatively a mirror could be positioned adjacent to the object being scanned to allow the beam to strike the mirror during the scan, but positioning the calibration mirrors away from the disk as shown in FIG. 3 is preferable since it reduces the number of fragile components near the mechanical moving parts. Having the maximum reference signal for comparison allows the amplitude of the reflected beam from the disk to be converted to an absolute measure of reflectivity. The signal from the calibration mirrors can be used as a start of scan without using it as an absolute amplitude reference. Once the beam strikes the Calibration Mirror 21 the reflected beam will slew to its maximum value. This transition from no reflected beam to the maximum forms a sharp edge in the analog output of the detector which can be used as the start of scan signal. A fixed delay can then be used to gauge the approximate time at which the scan line will be at the first data point on the disk. To avoid having false Triggering from the other transitions in the signal at the edges of the disk, the circuitry which detects the start of scan signal should delay resetting until the scan line has cleared the last edge of the disk.

Figure 4:
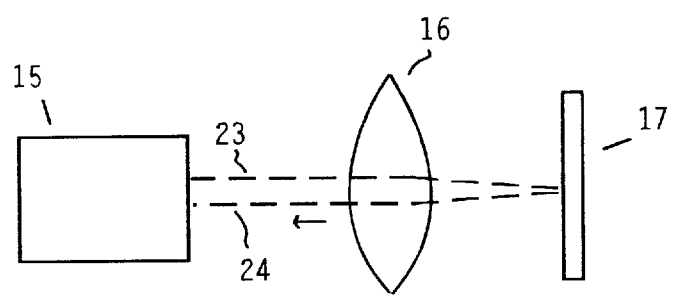
FIG. 4 shows the spatial relationship between the incident beam and the reflected beam between the surface and polygon mirror.
Figure 5:
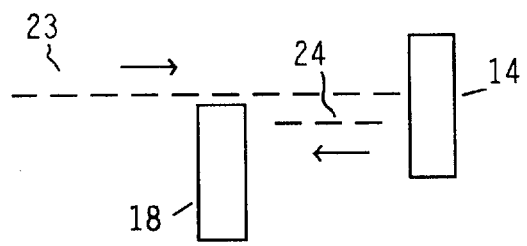
FIG. 5 shows the spatial relationship between the incident beam, the reflected beam and the capture mirror.

FIG. 4 shows the preferred spatial relationship between the incident beam and the reflected beam between the surface 17 and polygon mirror 15. As previously noted the reflected beam 24 is offset from the incident beam 23 to allow the reflected beam to be routed to the detector. This is achieved by causing the incident beam to strike the surface at a slight angle which causes the reflected beam to come off at a slight angle as shown in the FIG. 4. As an example, an offset angle of a few degrees over a 125 mm path results in a beam offset of on the order of 5–10 mm which easily allows the reflected beam to be routed to a mirror which is by-passed by the incident beam. The telecentric aspect of the TLA causes the reflected beam 24 to be essentially parallel to incident beam 23 after the reflected beam has passed through the TLA. The optical axis of the TLA should ideally split the angle formed by the incident and reflected beam at the surface to minimize the effects of coma and spherical aberration due to the beam separation. FIG. 5 shows the spatial relationship between the incident beam and the reflected beam in relation to the Capture Mirror 18 and Steering Mirror 14. The incident beam 23 passes above the Capture Mirror 18 on its way to Steering Mirror 14. The reflected beam 24 is sufficiently offset to allow it to strike Capture Mirror 18 and to be routed to the detector. This arrangement is deemed superior to using a beam splitter with the signal losses associated therewith. It is feasible to allow the incident and reflected beam to be coincident until the reflected can be separated using an appropriate beam splitter, but the arrangement shown is deemed preferable. Beam splitters which could be used if desired include polarizing beam splitters, partially reflective beam splitters, or pellicle beam splitters.

Figure 6:
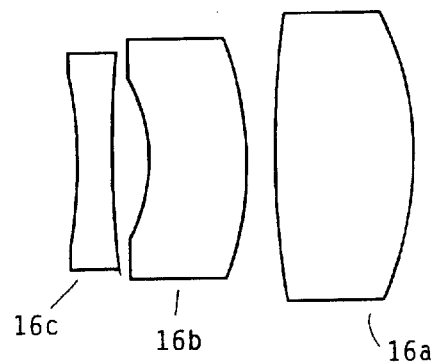
FIG. 6 shows a representative three lens implementation of the telecentric lens assembly.

The TLA's characteristics are tailored to the specifics of the application and particularly to the size of the surface being inspected. One standard size of disk for use in disk drives is 95 mm in diameter. For such a surface the design of the TLA could be specified for the wavelength of the laser being used as a field of 105 mm, focal length 125 mm, telecentricity<0.5 degrees and field curvature of<1.0 mm. FIG. 6 illustrates a three element spherical lens implementation which can be used to meet these requirements. Other implementations (including a single lens) may be used. An optical configuration which is capable of scanning 95 mm disks is also capable of being used to scan smaller disks. When smaller objects are being scanned it may be desirable to increase the sampling rate in order to obtain the same number of pixels for the smaller object.

Figure 7:
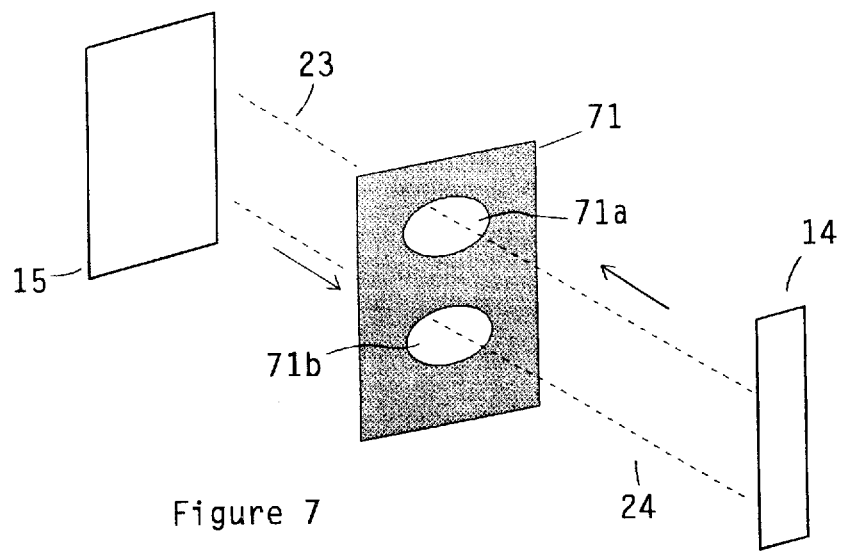
FIG. 7 shows an alignment aperture mask.

FIG. 7 shows an optional aperture mask 71 having apertures (holes) 71a and 71b which is positioned between scanner 15 and mirror 14 so that the incident beam 23 passes through aperture 71a and reflected beam 24 passes through aperture 71b. The aperture mask is made from opaque material and the apertures are sized to limit the cone of scattered light that passes through. Limiting the cone of the reflected beam is more important than for the incident beam. The reflected beam cone size should be limited to removing some of the near forward scattered light to improve the sensitivity of the detector to reflected light. The size of the aperture for the reflected light should be selected empirically for the particular application by scanning a surface feature known to produce near forward scattered light, e.g., laser texture bumps on disks. The aperture should not be overly restrictive, however, since variation in the polygon faces, etc. will cause some tolerances to exist in the reflected beam. Using an aperture of approximately six times the diameter of the beam in the arrangement shown was found to result in a superior detection capability for the laser texture zone. The masking of the near forward scattered light can be performed at various points in the path of the reflected beam, e.g. at the detector, but the position of the aperture mask as shown has the additional benefit of providing an aid for coarse alignment of the beams which should be positioned in the center of the apertures. Optionally, a removable translucent member may be placed over the apertures to enhance the visibility of the beam position during alignment.

Various other alignment features and aids may be incorporated into the design of the LIT. For use in a manufacturing environment it is important that alignment be easy to obtain and to maintain. In a two channel implementation the disk must be centered between the two TLAs and be perpendicular to the horizontal axis of the system. The position of the disk holder with respect to the optics board is adjusted, then the distance position along mounting rail of the TLAs is adjusted. Preferably several of the components in the optical path will have x-y adjustments, but it is not required that they all have adjustments. The lenses 12, 13 comprising the telescope are likewise mounted on rails to allow the distance between them to be adjusted to control spot size. At least one of the lenses in the telescope should preferably have a fine position adjustment.

The apertures in the aperture mask may also be used during the finer alignment process by positioning target plugs in the apertures which have small diameter alignment holes, e.g. 1 mm in diameter, positioned at the central point where the beams are properly aligned. One or more similar targets with alignment holes may be used in the path from the laser to the steering mirror. If the laser and the telescope lenses are mounted on an optical rail, one or more targets with alignment holes can be placed on the rail and moved along the rail if desired to aid in the x-y alignment of the laser. The approximate alignment of the beams can be observed visually since misalignment will reduce the intensity of the beam passing through the small holes. After coarse alignment has been achieved, the amplitude of the beam as measured by the detector 19 provides a precise aid for alignment of the entire path. The x-y adjustments of the laser, the steering mirror, etc. are used to achieve maximum amplitude of the output signal at the detector from a reference disk having at least a portion which is used as a defect free standard.

The TLA determines the spot focusing and telecentricity of the beam. Telecentricity is determined by the spacing of the TLA to the polygon and is set using the scan lens micrometer which translates the TLA along the axis between the polygon and the disk. The input beam collimation of the incident beam entering the TLA is set by adjusting the spacing between lenses 12 and 13 of the telescope. The circularity of the return beam after reflection from the polygon is a function of the telecentricity and can be used during alignment. Spot size should be reasonably constant through a scan, so spot size should be measured across the scan field using a spot size measuring instrument positioned in the scan plane at multiple scan positions. If the deviation in spot size is too large, additional alignment is needed.

Calibration Disks

A calibration disk or disks with precise laser marks may also be used to simulate scratches to further calibrate the tool so that the various LIT tools will provide repeatable and comparable results. For example, a circular "scratch" of precise width (i.e., a fixed number of pixels) is formed by laser into a set of calibration disks then each system can be adjusted to detect the correct number of pixel defects. This is accomplished by producing a standard, laser-produced feature on a reference disk. The feature is a ring produced by continuous exposure of a focused CO2 laser onto a glass disk. The glass disk is vacuum mounted onto a spindle which is rotated under the focused beam. By adjusting the exposure parameters (laser power, spindle rpm and exposure duration) the height and width of the ring cross-section is adjusted to produce a signal level in the range of the defects of interest. A typical set of parameters is approximately 50 mW laser power, 15 rpm spindle speed and 1 second exposure. The laser-exposed glass disk is then coated with a standard metallic/magnetic coating of a thin film disk of the type to be inspected. This will produce the same reflectivity and thus, optical signal as is obtained when inspecting the actual disk product.

For calibration, the calibration disk is scanned by the LIT using a special calibration program. This program has a mask adjusted to measure the laser-produced ring inside a standard annulus. The defect pixels within this annulus are measured and compared to the desired value. This calibration technique incorporates a simple way to determine inspection tool variation. Any variation in tool parameters affecting the normal pixel count such as optical alignment, laser power drift, lifter variation, mechanical stability, etc. will be detected in the scanning of the calibration disk. This serves as a simple means to verify constant performance of the surface inspection The tooling for producing laser zone texture on glass disks can be used to produce the calibration disk. The formation of laser zone texture on NiP/Al:Mg disks and glass disks both use a pulsed laser to produce a spiral array of microscopic texture bumps in a well defined radial zone. However, because the absorption wavelength of glass is significantly different from NiP-coated metal disks, the glass texture process utilizes a carbon dioxide laser (CO2). For the laser texture process for glass, a specially designed CO2 laser is used which emits radiation at a non-standard 9.25 microns wavelength. This wavelength is specified since the aluminosilicate glass disks utilized for drive manufacturing have their peak absorption near this wavelength. The laser texture tool for glass utilizes a temperature-stabilized, continuous-wave, CO2 laser which is modulated (i.e. pulsed) by an acousto-optic modulator (AOM). Two identical beams are emitted from the AOM which form the two radiation channels for performing simultaneous double-sided texturing of a disk. The AOM is used to control both the beam intensity, and the pulse duration. The pulsed laser light is passed through a focussing lens prior to impinging on the disk in a spot size that can vary from 30 to 100 microns. The pulse duration can be varied between 1 and 10 microseconds. Each laser pulse produces 1 texture bump. The radial texture zone is produced by simultaneously spinning and translating the hub-mounted disk.

Since the glass texture tool is capable of producing "defects" (i.e. texture bumps) on smooth glass surfaces, it was reasoned that this defect could repeatably and controllably be placed on a glass disk. Further, if the defect was found to provide a sufficient and repeatable signal for the LIT process, then the glass texture tool could provide means for fabricating calibration disks. To create the calibration disk, the disk was rotated, but not translated, during the laser exposure. This produces a circular defect whose radial width was approximately 10 to 20 microns. Various pulse durations and pulse repetition rates were investigated, ranging from continuous-wave "scribing," to forming perforated marks by utilizing 16 millisecond pulses at 25% duty cycle, to forming defects by using 1 microsecond pulses at 20 kHz repetition rate. The LIT signal level could be increased by forming the circular defects at higher laser intensity levels, by utilizing longer exposure periods for a fixed intensity, or by reducing the disk spin rate. After testing many disks, a "best mode" procedure for defect production was determined. The disk onto which the defects are to be fabricated is mounted on the hub and spun at a rate of 15 revolutions per second. By varying the radial position of where the laser light strikes the disk, say from 20 mm to 30 mm, the LIT signal level from the fabricated defect can be made to decrease. By using a shutter in the laser beam path, precise 1 second exposures are produced on the disk. The laser is pulsed at 20 kHz, and the pulse duration is 1 microsecond. The average laser power incident on the disk varies between 50 and 100 milliwatts, depending upon the desired signal level of the produced defect. In operation, once the shutter is opened, the laser beam is passed through a beam expander to increase its size to approximately 7 mm diameter. The expanded beam is then passed through a 25 mm focal length lens prior to being focussed onto the disk. The estimated focal spot size is 30 microns which produces a bump diameter of about 10–20 microns. Because of the gaussian nature of the focussed beam, the produced defect has a width less than the focal spot size. The range for the diameter of the bumps should be about 10 to 40 microns which also defines the width of the circular feature. A typical range for the height of laser formed bumps is on the order of 15–50 nm. The exact dimensions (width and height) of the defect depend on parameters such as intensity level, spot size and linear velocity of the spinning disk. At 1 sec. of exposure, and a disk spin rate of 15 rps, 15 revolutions of the disk are made past the focussed laser spot. After this time, the shutter is closed and the process terminated. Since each pulse is producing a discrete texture bump (as described above), the fabricated circular defect consists of approximately 20,000 such bumps circumferentially overlapped around the disk, and all at the same radius.

Polygon Synchronization

Figure 8:
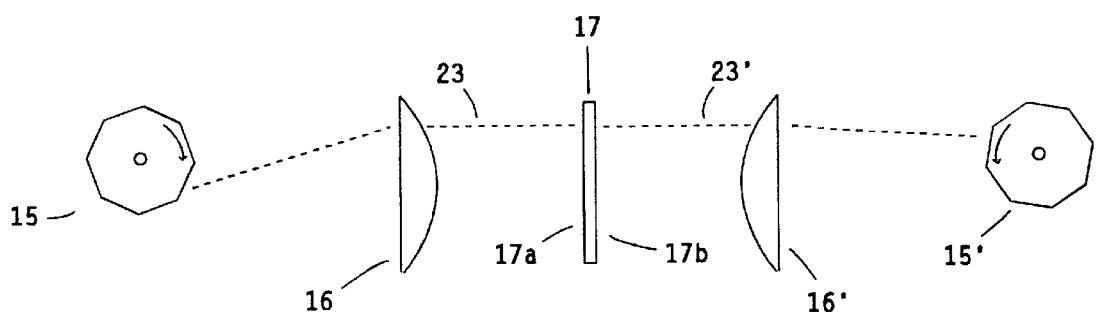
FIG. 8 shows the polygon scanner orientations in a two channel embodiment.
Figure 12:
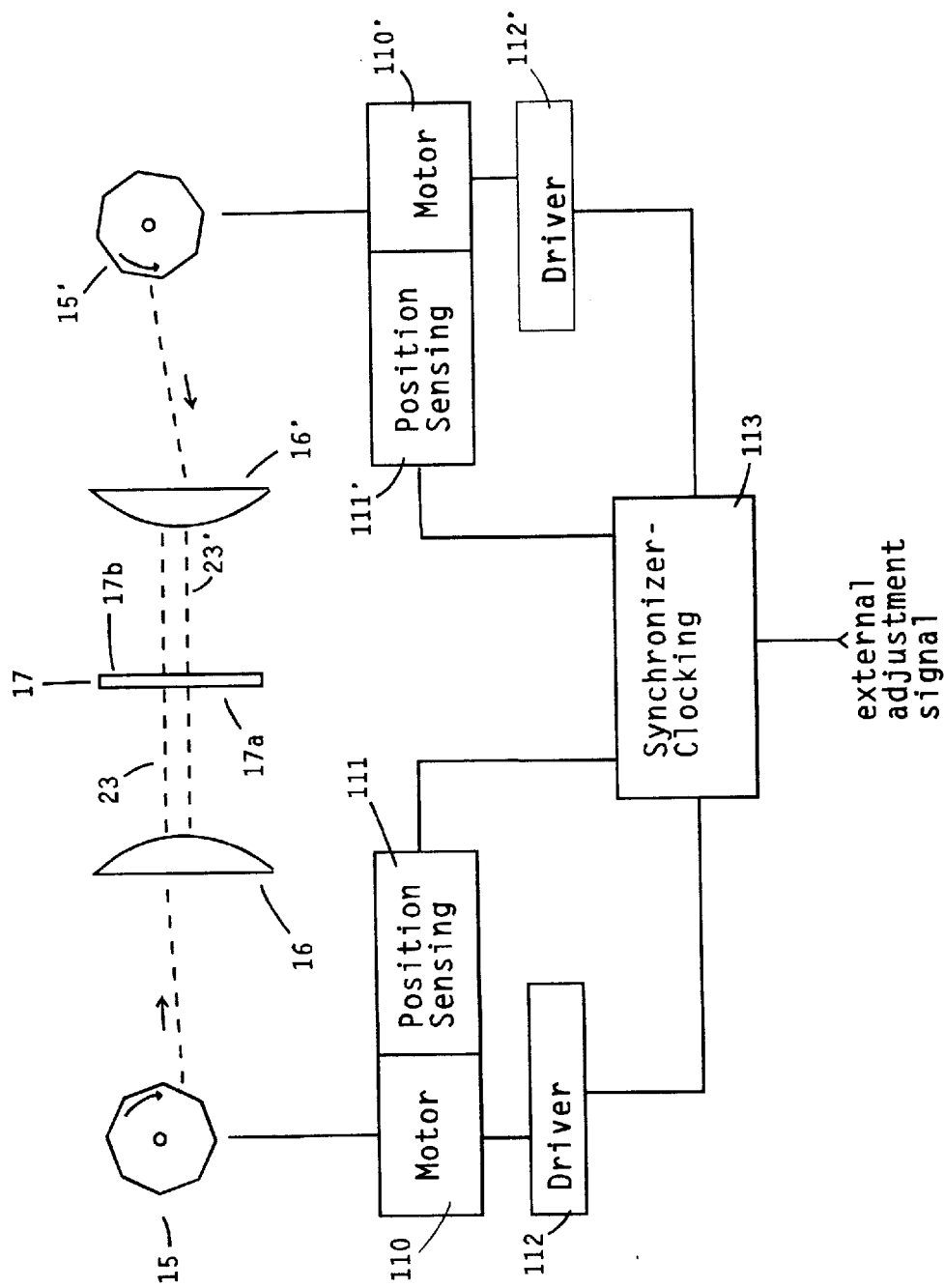
FIG. 12 illustrates a control system for synchronizing and offsetting the rotation of the polygon scanners.

In a two channel implementation of the invention, i.e., a LIT which inspects both planar surfaces of a disk simultaneously, there are several options on how the A and B-beams can be spaced and coordinated with each other. Interference between the channels will occur when the beams pass through the central hole in the disk unless steps are taken to prevent it. A similar problem might arise if the LIT is being used to inspect any object having holes and/or transparent portions. The polygons can be arranged to rotate in a common direction which will result in the scan on each side of the disk proceeding in opposite directions and crossing in the center of the scan area. When the beams cross there will be crosstalk as the beam from the opposite channel reaches the detectors. One arrangement to minimize interference has the B-beam vertically displaced from the A-beam, but this causes difficulties in building the tool and coordinating the data. A preferred arrangement is shown in FIG. 8. FIG. 8 shows the polygon scanner orientations in a two channel embodiment where the polygons 15, 15' are coplanar, but spin in opposite directions which results in the two beams 23, 23' maintaining a fixed relationship to each other as they scan. In a preferred embodiment the rotational position of the two polygonal scanners are synchronized, but with one being advanced or retarded in time to avoid interference when the beams scan across the hole in the center of the disk. The beams will still pass through the hole in the disk and be reflected off of the opposite channels polygon, but will be sufficiently separated from the path of the reflected beam to be diverted away from the detector. FIG. 12 illustrates a control system for synchronization and offset of the polygons. Beams 23, 23' are shown passing through the hole in the disk. The beams are only shown up to the TLAs 16, 16' but each will of course pass through the transparent lenses and be reflected from the polygon facet. The separation between the beams is shown greatly exaggerated so that the offset is clearly visible. The polygons are rotated by DC motors 110, 110' which have integral position sensing units 111, 111' which can provide index pulses as well as a binary value indicating the angular position of the motor. The positional signals are fed back into the Synchronizer/Clocking unit 113. This provides signals to the motor drivers 112, 112' which control the speed and phase of the motors. Using the position feedback and an external input, the Synchronizer/Clocking unit retards or advances the phase of one of the motors (e.g. motor 110') to allow magnitude of the offset between the two motors to be controlled while maintaining the same rotational speed. The external input signal can be as simple as pulse generated by an operator pressing a switch which causes the phase to advance a few microseconds for each pulse. One convenient way to set the offset is to adjust for zero crosstalk. An operator could do this by observing an oscilloscope trace of the output of one detector and bumping the phase switch until the signal is essentially zero for the hole area of the disk.

Mechanical System

Figure 9A:
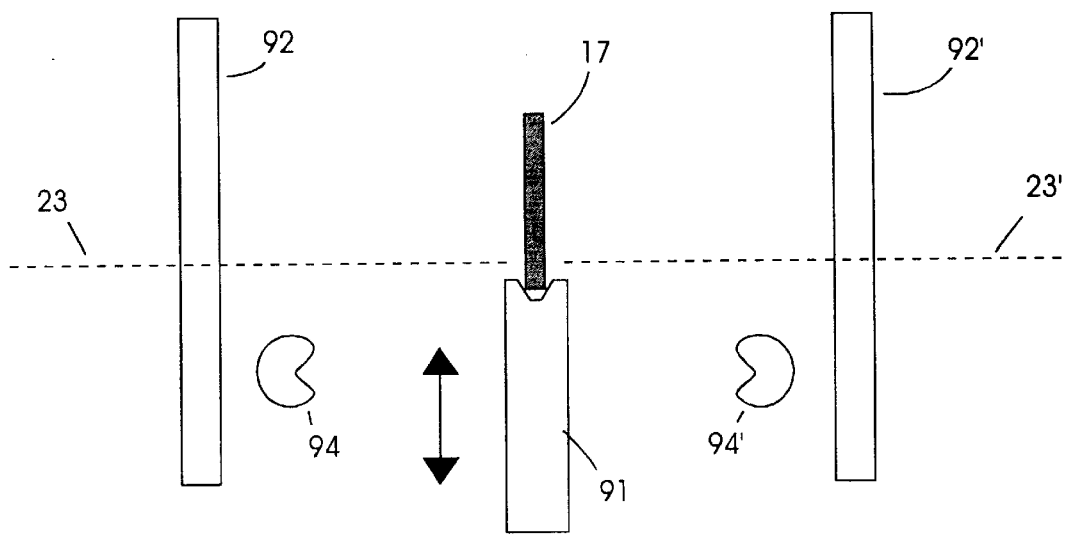
FIG. 9A and 9B show baffles and air knives in a inspection subcompartment and 9C shows the lifter supporting the disk.
Figure 9B:
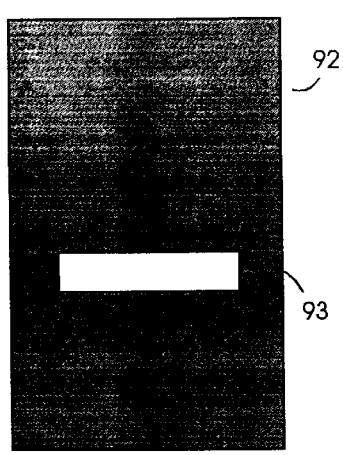
Figure 9C:
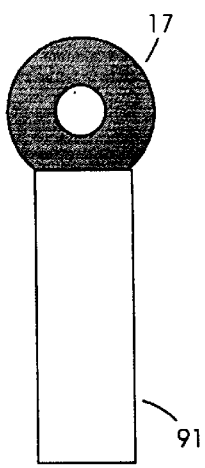

FIGS. 9A and 9B show air baffles and air knives in an optional inspection subcompartment which can be used in the LIT. FIG. 9A is a cross-sectional side view of the disk 17 being supported by the lifter 91 between the air baffles 92 and 92'. The frontal view of the disk and lifter is illustrated in FIG. 9C and the air baffle structure is shown in FIG. 9B. Each of the baffles has a beam port 93 which is a horizontal opening in the baffle through which beams 23 and 23' pass to strike the disk. The beam ports also provide a path for the air flow out of the inspection subcompartment. As shown the lifter 91 is a paddle-like member with a longitudinal slot in the top which engages the edge to support the disk in the vertical position without clamping. The lifter can be of any shape and design which allows the disk to be held without damage and moved through the scan line. For example, the body portion of the lifter could be a rod. The disk is supported from the bottom to use the weight of the disk to retain the disk in the slot and help eliminate any need for clamping. The cross section of the slot preferably has V-shaped sides and is curved to match the curvature of the disk. As shown the top of the lifter is rectangular, but alternatively can be V-shaped or curved to further minimize the amount of the disk surface which is obscured. The top of the lifter may also have fingers to hold the disk. The slot end portion of the lifter should be designed to obscure no more of the disk than is necessary to support the disk since it limits the available inspection area. A disk for use in a disk drive has a small band around the outer perimeter which is not used for recording which allows a small area to be obscured for support without reducing the effectiveness of the inspection. Although the lifter arrangement is considered preferable, any alternative mechanism(s) which provide the function of moving the disk into the inspection area and through the scan lines are feasible. The movement of the disk should be orthogonal to the scan lines, therefore, in the Described embodiment the scan lines are horizontal and the movement of the disk is vertical, but if the scan lines are vertical, then the movement should be horizontal. Other examples of means for moving the disks in and out through the scan lines include a conveyor system or any type of mechanical arm. The curved v-slot can be used to support the disk in combination with any appropriate movement system, but it is also possible to grip the disks by the edges.

The preferred embodiment is shown as a two channel system which inspects both sides of the disk simultaneously. Alternatively, a single channel system could be used to inspect both sides of the disks either by having the mechanical system flip the disk around and repeat the scan on the second side of the disk or by splitting the scanning beam and using additional mirrors to direct the split scanning beam to the second side of the disk.

The air knives 94, 94' are used to direct a shaped stream of partially ionized air onto each surface of the disk as it moves into the subcompartment. The air knives are nozzles which form a fan shaped air flow pattern which strikes the disk surface in a cross section of relatively narrow height, but with a width extending across the diameter of the disk. The action of the air streams is to blow off loose particles from the surfaces which might otherwise be detected as a defect in the disk. If the scan is performed when the disk is moving downward, then the entire disk will have passed through the air knives prior to the start of the scan. It is preferable to turn the air knives off when the scan is actually being performed to minimize vibrations which might introduce noise into the data. It is also preferable that the air knives provide approximately equal force on the surfaces of the disk so that the net force on the disk is minimal and the disk can be supported without clamping. Preferably the air coming into the subcompartment will be relatively clean. In addition to optionally operating the LIT in a clean room environment, additional filtering may be advantageous. For example, a HEPA filter may be conveniently installed above the subcompartment so that filtered air can be forced into the top of the subcompartment and out of the beam ports in the air baffles. There will also be a slight air flow out of the bottom of the subcompartment through the entrance port used to lift the disk into the subcompartment to help reduce contamination from other parts of the apparatus.

Automatic Feeding System

Figure 10:
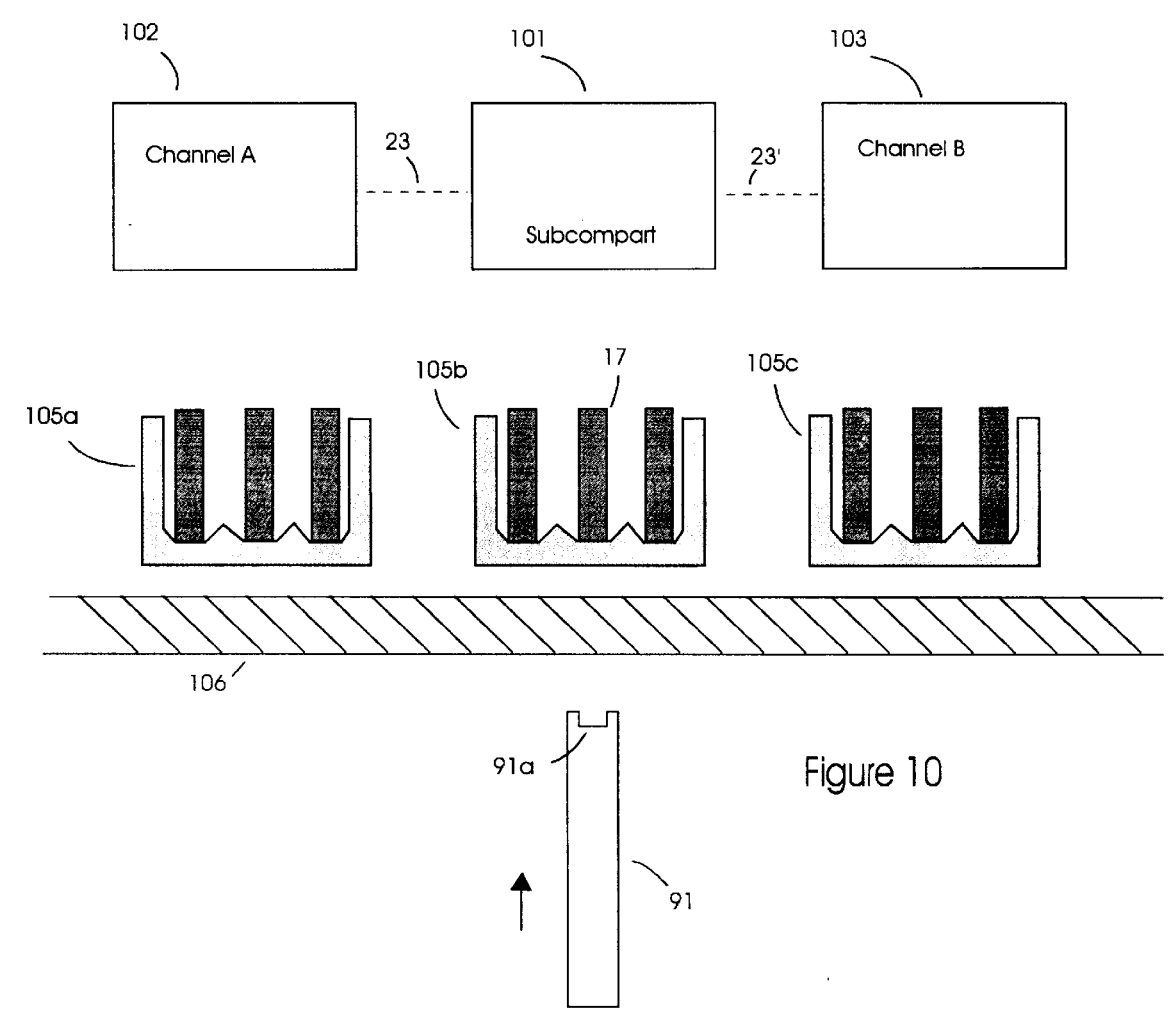
FIG. 10 shows the relationships between the conveyor, the lifter and the subhousing.
Figure 11:
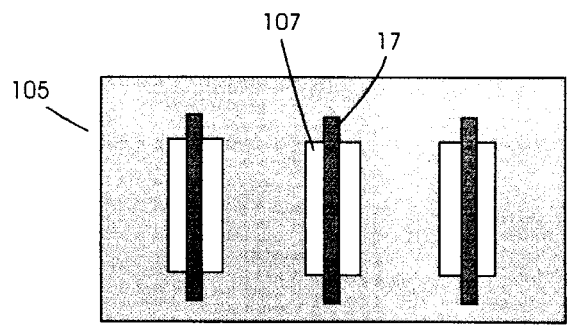
FIG. 11 illustrates a top view of the disk carriers.

The following section describes an embodiment of a system for automatic feeding of disks into the inspection area. Disks could be placed manually or by robot arm in the lifter, but for high volumes it is clearly preferable to have a simple but efficient automatic feeding system similar to one described below. Operators feed the tool by placing groups of disks in plastic carriers 105*a*–*c* on a conveyor belt 106. The carriers move along the conveyor belt underneath the actual laser apparatus until they reach the loading point where a lifter picks the disks up out of the carrier and pushes it up into the path of the air knives and the scan lines. FIG. 10 shows the relationships between the conveyor 106, the lifter 91 and the subcompartment 101. The disks 17 are brought into position over the lifter by being moved in disk carriers 105a–c placed on the conveyor system 106. When a disk is in position the lifter extends up through the conveyor, through an opening 107 in the bottom of the disk carrier to engage the disk 17. FIG. 11 shows the top view of a disk carrier 105. The slot 91a in the top of the lifter engages the bottom edge of the disk and lifts it out of the carrier up into the subcompartment 101 where the scan occurs. The extension range of the lifter must therefore be large enough to move from its initial position below the conveyor to a point at or above the scan line which will probably be equal to several times the diameter of the disk. The speed at which the lifter moves the disk through the scan line is a parameter which needs to be coordinated with the scan rate and the signal processing. Once established the movement rate should not vary.

The conveyor 106 must have sufficient sections and controls to position a disk carrier so that the first disk is over the lifter, then pause while the disk is lifted out and returned. If there are multiple disks in the carrier, the conveyor must index to the next disk and repeat the process for each disk in the carrier. The conveyor functions may De controlled by the same computer which processes the scanned data, but the functions are sufficiently simple to allow use of a standard programmable controller. When one carrier is finished it must be moved to an unloading area. Since the lifter must extend up through the conveyor, the conveyor must have openings which are always under the disk at the lift point. This could be done with spaced slats, cutouts, louvers, removable slats, a bulldozer type dual track system with a gap between the tracks, etc.

The disk carriers are shown with three disks, but could be designed for any number of disks including one. The requirements are that the disks be held sufficiently upright to engage the slot in the lifter and, of course, that there be clearance for the lifter to enter through the bottom to lift the disk out of the carrier. The curved v-slots as described for use in the lifter can also be used in the carriers with a slot on each side of the carrier to support each disk. The carriers can conveniently be made of plastic.

Data Capture and Analysis

Figure 13:
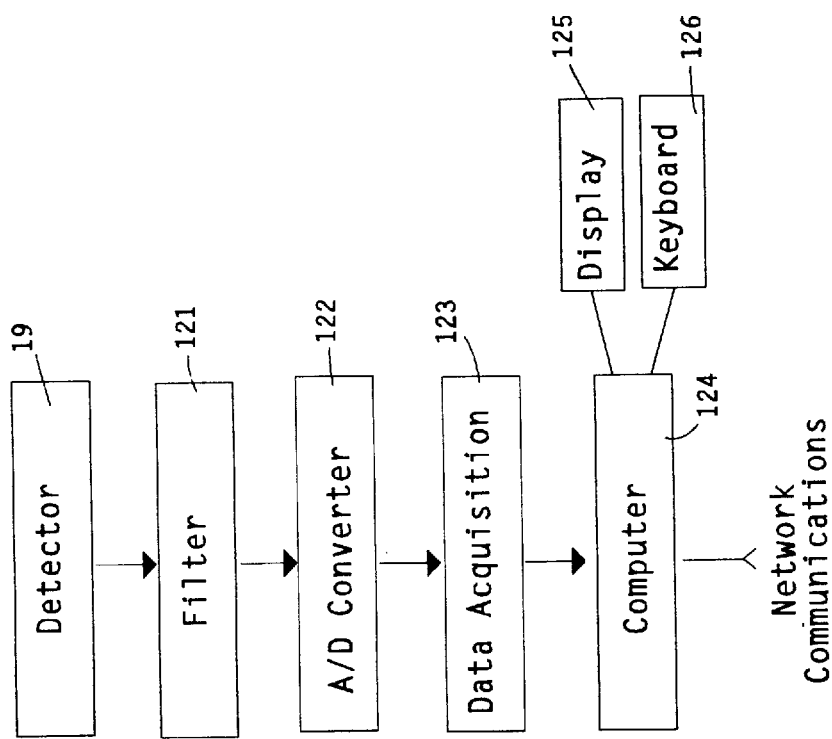
FIG. 13 illustrates the data acquisition path.

FIG. 13 illustrates a possible data acquisition path for one channel of an LIT. The analog signal from the detector 19 is optionally filtered by filter 121 before being sampled and digitized by the A/D converter 122 to get a value for the reflectivity at the sample points. The sampling rate should be selected in coordination with the time required for each scan line and the desired resolution. For example, if the usable portion of each scan line requires 1 ms and a resolution of 2000 pixels per line is wanted, then a sampling rate of 2 MHz is needed. The spacing between the scan lines is the distance that the disk moves vertically during one scan. If 2000 vertical pixels are desired for a 95 mm disk, then the vertical movement should be about 47.5 microns per scan. Each digital sample value represents one pixel in the image of the surface of the disk. The data acquisition hardware 123 places the pixel data in a buffer which is accessible by the computer 124. Since the surface is scanned in lines, the pixel data is organized into lines as well. Since data acquisition is a common requirement, there are commercially available cards which can be plugged into slots in a PC, e.g., PCI bus slots, which will perform the required function at a sufficiently high rate. The A/D unit may also be included on such a card. The computer which processes that data can be any general purpose computer or workstation which has sufficient speed to process the data in the time allowed, e.g., within a few seconds. The data acquisition path for the data from the second channel, if present, should be identical to the one shown. The computer can process the data for the two channels if it is fast enough, but it is also feasible to use separate computers for each channel. If separate computers are used, the results can be communicated from the B-channel computer to the A-channel computer which can then act upon the consolidated results by rejecting the disk or reporting the results through the network communication facilities to the master floor control system. At least one computer in the system should have a display 125 on which the enhanced image(s) can be displayed as well as messages, etc. Similarly at least one keyboard 126 should be available to allow parameter entry, manual control, maintenance, etc.

If the optional calibration mirrors are used, then the first portion of each scan line will correspond to maximum reflection and can be used as a reference signal for finding absolute reflectivity and as a start of scan signal for the hardware. The means for sampling and digitizing the analog signal will generate pixel data stored in a buffer which will contain a digital value for the intensity of the reflected calibration beam and a plurality of pixel values representing the intensity of the reflected beam for a line on the first planar surface of the disk; and the data analysis means will compare the digital value for the intensity of the reflected calibration beam to the plurality of pixel values to determine an absolute reflectivity corresponding to each of the plurality of pixel values. The abrupt signal change which corresponds to the edges of the disk can be used to find the position of the edges in the line of data. For lines which cross the central hole in the disk there are four edges, otherwise there are two edges per line. Since it is not desirable to test 100 percent of the surfaces of the disks, provision has been made to exclude portions of each line by use of a mask. This could be done on a pixel by pixel basis with a flag bit for each pixel indicating whether it should be processed or not, but this method requires a relatively large amount of storage. A preferable approach is to record start and stop points in a table for each scan line. Using four lumbers per line, e.g. x1, y1, x2, y2 allows the software to exclude the first x1 pixels in the line on the disk from processing, then process all pixels until pixel y1 is reached at which point processing is suspended again until pixel x2 and then continues until pixel y2 where processing of the line stops. The set of these numbers corresponding to the shape of the image of the disk being scanned will be called the mask. Since the mask is referenced to the edge of the disk, it must be located on pixel data in the buffer. The image of the disk in buffer does not always appear at the same place for various machines, times, etc. and, therefore, there is a need to fit the mask to the particular data by finding (or predicting) the location of the edges. Note that even though the disks are circular it is possible that the image of the disk may be elliptical due to artifacts of the system. For a line with only two edges and no laser bump texture only two numbers are required in the mask, since there is no need to skip over an area in the center of the disk, but it may be convenient to have four numbers for each line for simplicity. If an object other than a disk with a single central hole were to be scanned by the system, the mask could be adjusted accordingly by adding or removing numbers to cover the maximum number of the starts and stops required.

Figure 14:
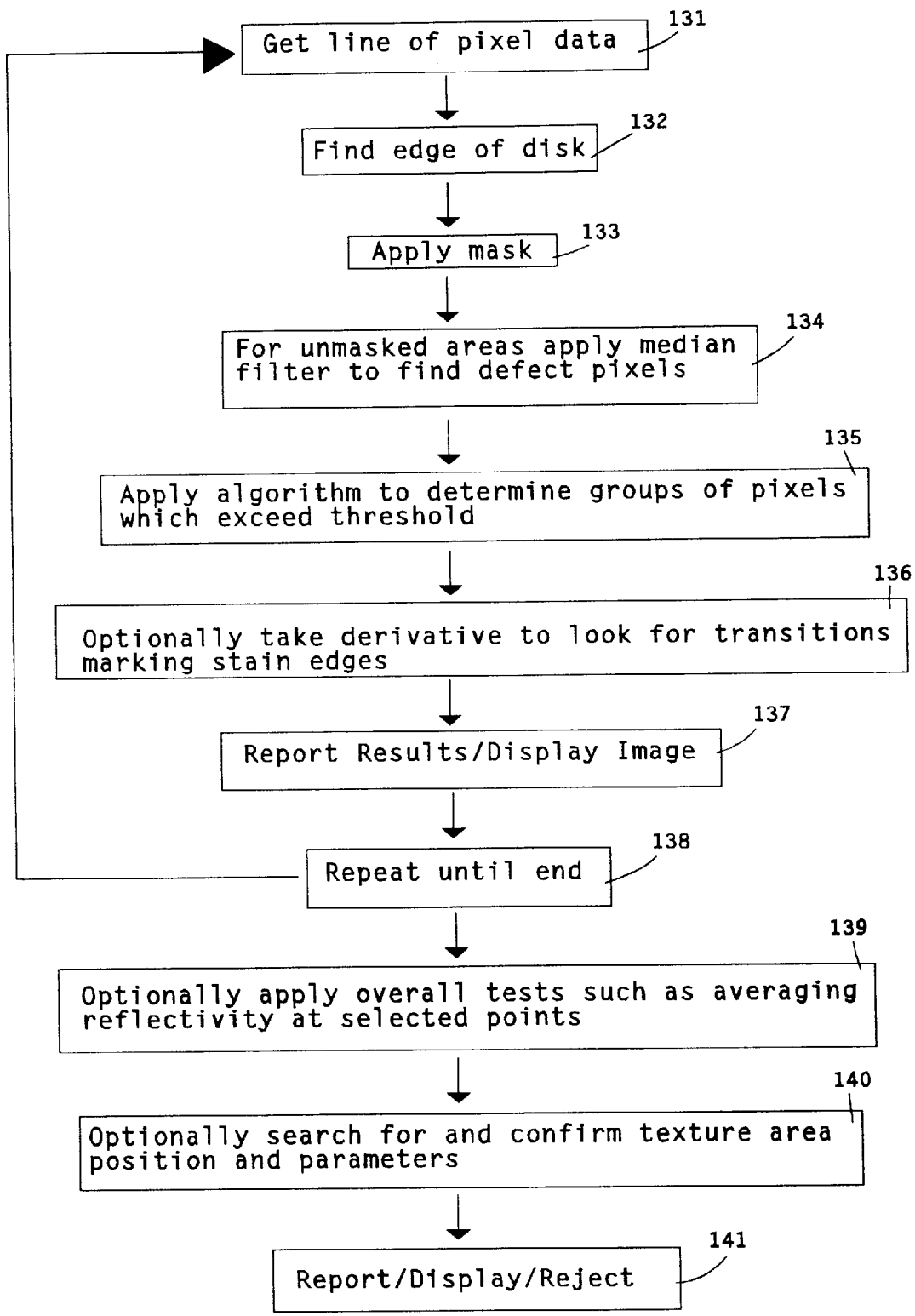
FIG. 14 is a flow chart of the data analysis.

FIG. 14 is a flow chart for the data analysis. Initially the data is processed one line at a time, so the pixel data is read line-by-line 131 and the line process is repeated until the last line 138. The edge of the disk in the line is found 132. The mask is applied to the line starting with the edge 133. The unmasked portions of each scan line are processed for defects by use of median filter 134. A selected number of pixels (e.g. 30–150) in a sliding window are averaged. A threshold above and below this running median is used to define a defect pixel. This threshold should be selected empirically at a level which most accurately finds true defects. A deviation of only a few percent (e.g. 3–4%) might be appropriate for a very uniform surface of a disk. However, single defect pixels are not generally significant for disks and may only be noise, so it is desirable to define an additional filter which looks for groups of defect pixels. Requiring that a predetermined number (e.g. 5–10) of consecutive defect pixels might be a simple way to achieve this, but could be sensitive to signal to noise problems. It is preferable that consecutive pixels not be required. A preferable analysis looks at the total number of defects in a selected region which can be a sliding window. The appropriate parameters for the window size and percentage of defect pixels which are tolerable should be determined empirically based on the particular application. The selected parameters should be programmable by operator input, but, or example, setting the threshold to 6 defect pixels out of a 3×3 pixel block might be typical for a magnetic disk scanning application. It has been found, however, that as the signal to noise ratio of the system increases, the need for a regional determination decreases. Another way to look at the data is to compute the maximum defect region size for the entire surface and compare this size to a selected threshold. Any standard statistical analysis of a pixel group of any size up to the entire surface which determines the probability that a particular deviation is due to chance can be used. A practical application of the LIT will probably use multiple tests of the sort described to define any number of defect signatures in the pixel data. Because the thresholds may need to be changed and experiments done to find the optimum value, they should be made programmable by operator input.

One optional method for looking for defects is to find the rate of change in the reflectivity using the derivative of the pixel stream. It has been discovered that a particular type of disk defect called a stain is not detectable using the median filter described above, but is detectable using the derivative because they are associated with a rapid change in reflectivity from one level to another 136. The second level of reflectivity persists for a relatively large distance so it is not seen as a defect using the median filter. Thresholds for the rate of change to be detected as a defect should likewise be defined empirically and be programmable.

Some, but not all, disks have a circular band a few millimeters around the hole which has been intentionally roughened (textured) by creation of thousands of small bumps to form a contact start/stop zone for a slider in a disk drive to physically contact whenever the disk is not spinning fast enough to fly the slider. Since these bumps are large enough (tens of nanometers) to be considered defects if located in the data area of the disk, the textured area must either be excluded from processing or processed using different parameters from those applied to the data area. The texture area can be detected by the presence of a small but sharp decrease in the reflectivity of the surface. This sharp transition is found by calculating the spatial derivative everywhere in the expected region for the texture and is then sorted to find the maximum and minimum values. It may also be useful to average several lines or areas of pixels in order to effectively increase the signal to noise ratio of the data. The disk qualifies based on the position of the texture area being where it should be and the change in reflectivity being within a selected range. The change in reflectivity can be correlated to bump geometry and provides a way to confirm that microtopography of the texture is correct 140.

For highest processing speed or greatest throughput, the data acquisition process and data analysis can be performed simultaneously or concurrently. In order to accomplish this, the data analysis must a) check for valid data and b) predict mask location in the buffer, before all edges have been discovered. The presence of valid data in the buffer can be ascertained by querying the data acquisition electronics for amount of data transferred (if that capability exists as it does in some commercially available systems) or by timing. Prediction of mask location is performed with the knowledge that the disk shape does not change from disk to disk and that only small changes in disk position will occur. Given this, the edges discovered in the first 10% of the disk image are used to adjust the mask positions within certain limits. The analysis of the data in the buffer can then proceed even though the scan of the disk is not complete.

A disk that is flagged as defective can be handled in various ways including simple reporting, displaying the image, calling an operator or rejecting the disk 141. It is, of course, possible to build the capability into the LIT to sort the defective disks from the passing disks. It is also feasible to simply record the test results by carrier serial number and disk position and place the defective disks back into the carrier along with the passing disks. The results data can be electronically communicated to a shop floor control system or some form of printout or other marker might be attached to the carrier. The data could then be used to sort disks at a later time. One advantage of delaying the actual sorting of the disks to a subsequent time is that it allows the final decision to take additional tests into account and, thereby increases the flexibility of the system.

Another optional test that can be applied to the pixel from a finished disk which has sputtered thin films (or similar surfaces) is to select a set of areas distributed over the surface which are composed of multiple pixels and determine the average reflectivity of each area 139. If the average reflectivity of the selected areas varies more than a selected threshold, it may indicate a failure of the sputtering process to uniformly coat the disk. This type of test must be tuned empirically to the specifics of the surface being inspected and the process by which the surface is created.

One alternative test that can be applied using the alternative embodiment of the LIT which provides for absolute measurement of reflectivity involves estimating the thickness of the hydrogenated carbon (C:Hx) overcoat which is typically sputtered onto thin film disks. Table 1 shows the relationship between reflectivity and thickness of a typical C:Hx coating used on a thin film magnetic disk with a cobalt alloy magnetic layer. Although the hydrogen content of a C:Hx film can vary depending on the deposition process and parameters, a table of reflectivities can be established for any particular composition being used and an acceptable range can be defined for the test. Using the Table 1 data, if the established range for an acceptable C:Hx overcoat for a particular disk type is 100–200 angstroms, then the reflectivity measured by the LIT should be between 0.51 and 0.575 for the disk to pass inspection. This method can obviously be extended to any other surface coatings whose thickness can be mapped to reflectivity.

TABLE 1

| Reflectivity | C:Hx Thickness (Angstroms) |
|---|---|
| 0.64 | 0 |
| 0.625 | 50 |
| 0.575 | 100 |
| 0.56 | 150 |
| 0.51 | 200 |
| 0.46 | 250 |
| 0.4 | 300 |

The LIT system described herein is capable of detecting defects without human assistance, but an optional feature provides a display of the enhanced image(s) of the disk surface(s). There are a virtually unlimited number of ways that the pixel and defect data can be displayed in the form of an image. Obviously the magnitude of the pixel data can be converted to display intensities and/or colors. The defect pixels and areas should be displayed in a distinguishable manner, e.g. red dots on a gray background. If the derivative option is being used, then the map of the derivative value could be displayed rather than or in addition to the absolute value of the pixels. The mask could also be displayed, as well as the identified textured area. Display of the data is considered to be a very powerful option which allows human pattern recognition to supplement and monitor the functioning of the tool when desired.

The various inventions described herein have been illustrated in their preferred embodiments, but variations within the scope of the inventions will be apparent to hose of skill in the art.

What is claimed is:

1. An apparatus for inspecting a planar surface of an object comprising:
    means for scanning a laser beam (the incident beam) over at least a portion of a first planar surface of the object in a scan line to generate a reflected beam;
    a first calibration mirror positioned to reflect substantially all of the incident beam during a segment of the scan line as a reflected calibration beam;
    a detector for converting an intensity of the reflected beam from the planar surface and the reflected calibration beam into an analog signal;
    means for sampling and digitizing the analog signal to generate pixel data stored in a buffer containing a digital value for the intensity of the reflected calibration beam and a plurality of pixel values representing the intensity of the reflected beam for a line on the first planar surface of the object; and
    means for comparing the digital value for the intensity of the reflected calibration beam to the plurality of pixel values to determine an absolute reflectivity corresponding to each of the plurality of pixel values.

2. The apparatus of claim 1 further comprising movable support for the object which moves the object perpendicularly to the scan line.

3. The apparatus of claim 2 further comprising a second calibration mirror arranged to steer the incident beam during a segment of the scan line to the first calibration mirror, the first and second calibration mirrors being arranged so that a total distance traveled by the incident beam to the first calibration mirror is approximately equal to a distance the incident beam travels to the first surface.

4. The apparatus of claim 3 wherein the first calibration mirror is positioned away from the object and is nearer to a lens through which the incident beam passes than to the object.

5. The apparatus of claim 2 the means for scanning a laser beam further comprising:
    a telecentric lens assembly including one or more lenses; and
    a rotating mirror for scanning the beam through the telecentric lens assembly and across at least a portion of the planar surface, the beam striking the planar surface at angle which is substantially perpendicular which causes a portion of the beam to form the reflected beam which passes back through the telecentric lens assembly and is reflected off of the rotating mirror.

6. The apparatus of claim 5 further comprising:
    an air knife for blowing partially ionized air onto the first planar surface; and
    an aperture mask arranged in the path of the reflected beam to block at least some near field scattered light from striking the detector.

7. The apparatus of claim 2 further comprising an air knife for blowing partially ionized air onto the first planar surface.

8. The apparatus of claim 1 further comprising means for comparing the absolute reflectivity to a table of reflectivities to determine a parameter of a coating on the object.

9. The apparatus of claim 8 wherein the coating on the object is hydrogenated carbon and the parameter is thickness.

10. The apparatus of claim 1 further comprising an aperture mask arranged in the path of the reflected beam to block at least some near field scattered light from striking the detector.

11. The apparatus of claim 1 further comprising means for determining a rate of change in the pixel values and applying a selected threshold to the rate of change in the pixel data to identify defects or features.

12. A method for inspecting a planar surface of an object comprising the steps of:
    scanning a laser beam (the incident beam) over a calibration mirror to generate a reflected calibration beam which is directed onto a detector which produces an analog signal proportional to the intensity of the reflected calibration beam;
    sampling and digitizing the analog signal proportional to the intensity of the reflected calibration beam to generate a digital value corresponding to maximum reflection;
    scanning the incident beam in a scan line over at least a portion of a first planar surface to generate a reflected beam which is directed onto the detector which produces an analog signal proportional to the intensity of the reflected beam;
    sampling and digitizing the analog signal proportional to the intensity of the reflected beam to generate pixel data stored in a buffer; and
    comparing the digital value for the intensity of the reflected calibration beam to the plurality of pixel values to determine an absolute reflectivity corresponding to a plurality of pixel values contained in the pixel data.

13. The method of claim 12 further comprising moving the object perpendicularly to the scan line.

14. The method of claim 13 the step of scanning the incident beam further comprising rotating a polygon mirror to scan the incident beam through a telecentric lens assembly and across at least a portion of the planar surface, the beam striking the planar surface at angle which is substantially perpendicular which causes a portion of the beam to form the reflected beam which passes back through the telecentric lens assembly and is reflected off of the polygon mirror.

15. The method of claim 13 further comprising blowing partially ionized air onto the first planar surface.

16. The method of claim 12 further comprising steering the incident beam during a segment of the scan line to the calibration mirror using a mirror arranged so that a total distance traveled by the incident beam to the calibration mirror is approximately equal to a distance the incident beam travels to the first surface.

17. The method of claim 16 wherein the first calibration mirror is positioned away from the object and is nearer to a lens through which the incident beam passes than to the object.

18. The method of claim 12 further comprising comparing the absolute reflectivity to a table of reflectivities to determine a parameter of a coating on the object.

19. The method of claim 18 wherein the coating on the object is hydrogenated carbon and the parameter is thickness.

20. The method of claim 12 further comprising blocking at least some near field scattered light from striking the detector by passing the reflected beam through an aperture mask arranged in the path of the reflected beam.

* * * * *